United States Patent [19]
Beck et al.

[11] Patent Number: 4,820,845

[45] Date of Patent: Apr. 11, 1989

[54] ALKYLATION OF 3(5)-CYANO-1H-PYRAZOLE-4-CARBOXYLIC ACID ESTERS

[75] Inventors: James R. Beck; James A. Aikins; Eddie V. P. Tao, all of Indianapolis, Ind.

[73] Assignee: Eli Lilly and Company, Indianapolis, Ind.

[21] Appl. No.: 32,662

[22] Filed: Apr. 1, 1987

[51] Int. Cl.$^4$ ............................................ C07D 231/14
[52] U.S. Cl. .................................................... 548/378
[58] Field of Search ............................................ 548/378

[56] References Cited

U.S. PATENT DOCUMENTS

| | | | |
|---|---|---|---|
| 2,429,575 | 8/1971 | Appleby et al. | 564/204 |
| 3,847,933 | 11/1974 | Tyler | 548/564 |
| 3,898,280 | 8/1975 | Pander | 71/92 |
| 4,589,905 | 5/1986 | Beck | 71/66 |

OTHER PUBLICATIONS

Chiu et al., *J. Org. Chem.*, 43(1), 61 (1978).
*Chemical Abstracts*, 80, 107972x (1974).
Evans et al., *Can. J. Chem.*, 34, 1271 (1956).

*Primary Examiner*—Robert W. Ramsuer
*Attorney, Agent, or Firm*—Douglas J. Taylor; Leroy Whitaker

[57] ABSTRACT

The present invention provides a process for selectively alkylating pyrazoles comprising reacting a 3(5)-cyano-1H-pyrazole-4-carboxylic acid ester with a $C_4$–$C_8$ alkene, or a $C_5$–$C_6$ cycloalkene substituted at the 1-position with a $C_1$–$C_4$ alkyl group, and a strong acid in a solvent which contains a strong electron withdrawing group. Also provided are new 3(5)-cyano-1H-pyrazole-4-carboxylic acid ester useful as starting materials in the process of the invention.

18 Claims, No Drawings

ALKYLATION OF 3(5)-CYANO-1H-PYRAZOLE-4-CARBOXYLIC ACID ESTERS

BACKGROUND OF THE INVENTION

U.S. Pat. No. 4,589,905 discloses the use of 1alkyl-5-cyano-1H-pyrazole-4-carboxylic acid esters as intermediates to carboxamide herbicides and algicides. The intermediates are prepared by a multi-step process which includes reacting an alkylhydrazine with an alkyl α-acetyl-α-(dimethylaminomethylene)acetate to produce a 1-alkyl-5-methyl-1H-pyrazole-4-carboxylic acid ester, followed by conversion of the 5-methyl group to a 5-cyano group.

This invention concerns synthesis of these intermediates by direct alkylation of pyrazoles. While pyrazoles can be alkylated by a number of methods, most methods alkylate at both ring nitrogen atoms, thereby producing a mixture of alkylated products that is often difficult to separate. An object of the present invention is to provide a process for alkylating certain pyrazoles predominantly at only one of the ring nitrogen atoms, resulting in essentially pure alkylated product. A second object of the present invention is to provide new compounds; namely, 3(5)-cyano-1H-pyrazole-4-carboxylic acid esters.

SUMMARY OF THE INVENTION

This invention provides a process for preparing 1-tertiary alkyl-5-cyano-1H-pyrazole-4-carboxylic acid esters of the formula

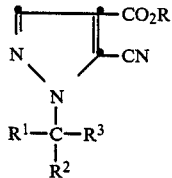

wherein:

R is $C_1$–$C_6$ alkyl; $R^1$ is $C_1$–$C_4$ alkyl; and $R^2$ and $R^3$ independently are $C_1$–$C_3$ alkyl, or when combined with the carbon atom to which they are attached form a $C_5$–$C_6$ cycloalkyl, with the proviso that when $R^2$ and $R^3$ are independently $C_1$–$C_3$ alkyl the total number of carbon atoms contained in $R^1$, $R^2$ and $R^3$ is $C_3$–$C_7$ comprising reacting a 3(5)-cyano-1H-pyrazole-4 carboxylic acid ester of the formula

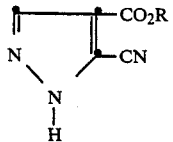

with a $C_4$–$C_8$ alkene, or a $C_5$–$C_6$ cycloalkene substituted at the 1-position with a $C_1$–$C_4$ alkyl group, and a strong acid, in a solvent which contains a strong electron withdrawing group.

In a preferred embodiment, the process employs alkenes such as isobutylene (2-methyl-1-propene), 2-methyl-1-pentene, 3-ethyl-2-pentene, or cycloalkenes such as 1-methyl-1-cyclopentene. The most preferred process employs isobutylene (2-methyl-1-propene) to produce a 1-t-butyl pyrazole.

This invention also provides new 3(5)-cyano-1H-pyrazole-4-carboxylic acid esters of the formula

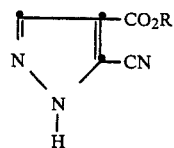

wherein R is $C_1$–$C_6$ alkyl.

The most preferred oompound of the present invention is 3(5)-cyano-1H-pyrazole-4-carboxylic acid ethyl ester.

DETAILED DESCRIPTION OF THE INVENTION

The following definitions refer to the various terms used above and throughout the disclosure.

The terms "$C_1$–$C_3$ alkyl" and "$C_1$–$C_4$ alkyl" refer to the straight and branched aliphatic radicals of 1 to 3 carbon atoms and 1 to 4 carbon atoms, respectively, including methyl, ethyl, n-propyl, isopropyl, n-butyl, sec-butyl, isobutyl, and t-butyl.

The term "$C_1$–$C_6$ alkyl" includes the foregoing groups as well as $C_5$ and $C_6$ groups such as n-pentyl, tert-pentyl, 3-pentyl, n-hexyl, and 2,3-dimethylbutyl.

The 3(5)-cyano-1H-pyrazole-4-carboxylic acid esters of this invention are prepared by reacting a 3(5)-carbamoyl-1H-pyrazole-4-carboxylic acid ester with a dehydrating agent. The carbamoyl starting materials are either commercially available, described in literature sources such as Jones et al., *J. Org. Chem.*, 20, 1342 (1955), or can be prepared by methods known in the art. Suitable dehydrating agents include phosphorus pentoxide, phosphorus oxychloride, phosphorus pentachloride, phosphorus trichloride, and thionyl chloride.

The 3(5)-carbamoyl-1H-pyrazole-4-carboxylic acid ester and dehydrating agent can be reacted with or without a solvent, as desired. If a solvent is employed it preferably will be identical to the solvent used in the subsequent alkylation reaction, thereby avoiding isolation steps. Additionally, an acid scavenger, such as potassium carbonate, may be added to neutralize any acids generated during the dehydration reaction.

The claimed compounds are useful as starting materials in the selective alkylation process of this invention. The alkylation may be accomplished by mixing a 3(5)-cyano-1H-pyrazole-4-carboxylic acid ester in a solvent which contains a strong electron withdrawing group. Such solvents include those having nitro or nitrile functionalities. Typical solvents routinely employed include nitroalkanes such as nitromethane, nitroethane, and 2-nitropropane, and alkyl nitriles such as acetonitrile, propionitrile, and butyronitrile. A preferred solvent is acetonitrile.

A co-solvent may be utilized when the alkylation reaction is conducted at temperatures at which the (3)5-cyano-1H-pyrazole-carboxylic acid ester starting material exhibits poor solubility in the solvent which contains a strong electron withdrawing group. The co-solvent aids in solubilizing the starting material, allowing the reaction to proceed at a faster rate. Chlorinated hydrocarbons such as methylene chloride, chloroform, and carbon tetrachloride are preferred co-solvents.

The concentration of 3(5)-cyano-1H-pyrazole-carboxylic acid ester starting material in the solvent mixture is not critical, but it is preferred to employ a sufficient amount of solvent to ensure that the alkylated product remains in solution throughout the reaction.

A $C_4$–$C_8$ alkene, or a $C_5$–$C_6$ cycloalkene substituted at the 1-position with a $C_1$–$C_4$ alkyl, is added to the solvent mixture, along with a strong acid. The $C_4$–$C_8$ alkenes employed in the present invention are all well known in the art and include alkenes such as isobutylene, 2-methyl-1-butene, 2-ethyl-1-butene, 2-methyl-2-butene, 3-methyl-2-pentene, 2,3-dimethyl-1-butene, 2,3-dimethyl-2-butene, 2-methyl-1-pentene, 2-ethyl-1-pentene, 2-methyl-2-pentene, 3-methyl-2-pentene, 3-ethyl-2-pentene, 4-methyl-3-heptene. The $C_5$–$C_6$ cycloalkenes employed in the present invention are also well known in the art and include such alkenes as 1-methyl-1-cyclohexene and 1-ethyl-1-cyclopentene. A preferred alkene is isobutylene. The alkene or cycloalkene and non-alkylated pyrazole starting material generally are employed in amounts ranging from approximately equimolar quantities to 50 moles of alkene or cycloalkene per mole of pyrazole, although the ratio of reactants is not critical. Typically the alkene or cycloalkene is employed in a slight excess relative to the pyrazole, for example from about 2 to about 8 moles of alkene or cycloalkene per mole of non-alkylated pyrazole.

The term "strong acid" refers to inorganic and organic acids, as well as the Lewis Acid zinc chloride. Examples of acceptable inorganic strong acids include sulfuric acid and hydrobromic acid. Typical organic strong acids include p-toluenesulfonic acid, methanesulfonic acid, and trifluoroacetic acid. Preferred strong acids include p-toluenesulfonic acid and sulfuric acid. The strong acid can be employed in either catalytic or non-catalytic quantities, since the amount is not critical. Typically the strong acid is employed in molar amounts ranging from about 5.0% to about 200.0% relative to the non-alkylated pyrazole.

The alkylation reaction is generally conducted at a temperature of about room temperature (25° C.) to about 125° C., with the most desired temperature being about 70° C. to about 120° C. Due to the alkene reactant's volatility, the reaction is normally run under pressure. The reaction pressure is not critical and will generally vary depending on the reaction temperature chosen.

The process is generally substantially complete after about 2 hours to about 40 hours when conducted at a temperature in the range of about 25° C. to about 125° C. The progress of the reaction can be followed, if desired, by standard high performance liquid chromatography (HPLC) analytical techniques.

The resulting 1-tertiary alkyl-5-cyano-1H-pyrazole-4-carboxylic acid ester can be isolated by standard methods, if desired, but need not be. The alkylated pyrazole is readily converted to a carboxamide herbicide or algicide by reaction with an amine according to the methods of U.S. Pat. No. 4,589,905.

The following Examples illustrate specific aspects of the present invention. The Examples are not intended to limit the scope of the invention in any respect and should not be so construed.

EXAMPLE 1

3(5)-Cyano-1H-pyrazole-4-carboxylic acid ethyl ester

To a 22 liter, 3-necked flask were added 5.72 liters of acetonitrile, 1,048 g (5.72 moles) of 3(5)-carbamoyl-1H-pyrazole-4-carboxylic acid ethyl ester and 791 g (5.72 moles) of potassium carbonate. The mixture was heated to 75–80° C. and 1,316 g (8.58 moles) of phosphorus oxychloride were added over one hour.

The mixture was stirred at about 80° C. for three hours then cooled to room temperature (25° C.), where stirring continued for an additional hour. The reaction mixture was filtered to remove potassium chloride salts and excess potassium carbonate, and the filter cake washed with 500 ml of acetonitrile.

The filtrate and acetonitrile wash were combined and the resulting solution concentrated to dryness under reduced pressure to provide solid 3(5)-cyano-1H-pyrazole-4-carboxylic acid ethyl ester. Cold deionized water (3 liters) was added to the solid and the mixture stirred for about 15 minutes, then filtered. The recovered solid was washed with 1 liter of cold deionized water and dried under vacuum at about 40° C. to provide 818 g (86.5% yield) of the above compound. m.p. 149–152° C.

EXAMPLE 2

1-tert-Butyl-5-cyano-1H-pyrazole-4-carboxylic acid ethyl ester

To a pressure reactor charged with 0.5 g (3.0 mmoles) of 3(5)-cyano-1H-pyrazole-4-carboxylic acid ethyl ester dissolved in 100 ml of acetonitrile were added 7.13 g (127.0 mmoles) of isobutylene and 0.2 g (1.0 mmole) of p-toluenesulfonic acid monohydrate. The reaction mixture was heated to 110° C. (pressure approximately 50 psig) and stirred for about 24 hours. The reaction was substantially complete, by HPLC analysis, so the reactor was vented to atmospheric pressure (0 psig). The solution was concentrated to an oil by removal of acetonitrile under reduced pressure.

Water (50 ml) and diethyl ether (100 ml) were added to dissolve the oil. The organic layer was separated and dried with sodium sulfate. The solution was filtered, and the solvent removed under reduced pressure to provide 0.66 g of 1-tert-butyl-5-cyano-1H-pyrazole-4carboxylic acid ethyl ester (91.8% yield). The product was shown to be 93.2% pure 1-alkylated pyrazole by HPLC.

EXAMPLE 3

1-tert-Butyl-5-cyano-1H-pyrazole-4-carboxylic acid ethyl ester

To a pressure reactor charged with 0.5 g (3.0 mmole) of 3(5)-cyano-1H-pyrazole-4-carboxylic acid ethyl ester dissolved in 50 ml of acetonitrile were added 7.13 g (127.0 mmole) of isobutylene and 0.2 g (1.0 mmole) of p-toluenesulfonic acid monohydrate. The reaction mixture was heated to 75–80° C. (pressure approximately 45 psig) and stirred for about 18 hours. The reaction was substantially complete, by HPLC analysis, so the reactor was vented to atmospheric pressure (0 psig). The solution was concentrated to an oil by removal of acetonitrile under reduced pressure.

Water (100 ml), diethyl ether (100 ml), and a saturated brine solution (100 ml) were added to dissolve the oil. The organic layer was separated, washed with 100 ml of water and dried over magnesium sulfate. The solvent was removed under reduced pressure to provide 0.66 g (91.8% yield) of 1-tert-butyl-5-cyano-1H-pyrazole-4-carboxylic acid ethyl ester.

EXAMPLE 4

1-tert-Butyl-5-cyano-N-methyl-1H-pyrazole-4-carboxamide

To a pressure reactor charged with 1,257 g of 96.1% pure 3(5)-cyano-1H-pyrazole-4-carboxylic acid ethyl ester (7.62 moles of ethyl ester) dissolved in 17,300 ml of acetonitrile were added 2,900 g (51.7 moles) of isobutylene and 483.15 g (2.54 moles) of p-toluenesulfonic acid monohydrate. The reaction mixture was heated to 85°-90° C. (pressure approximately 45 psig) and stirred for about 17.5 hours. The reaction was substantially complete, by HPLC analysis, so the reactor was vented to atmosphere pressure (0 psig) and the acetonitrile removed by distillation.

Aqueous methylamine (3,300 g of a 40%, by weight, solution of methylamine in water; 42.6 moles of methylamine) and methanol (3,810 ml) were added and the mixture was stirred at 50° C. for about 4 hours. The solution was allowed to cool to room temperature (25° C.), while stirring, overnight.

The solution was concentrated by removal of unreacted methylamine and methanol under reduced pressure. Cold water (7,600 ml) was added to the concentrated solution. 1-Tert-butyl-5-cyano-N-methyl-1H-pyrazole-4-carboxamide precipitated and was recovered by filtration. The carboxamide product, washed with 7,600 ml of cold water, was dried under vacuum at 40°-50° C. overnight to provide 1,316 g (84.7% yield) of essentially pure product.

EXAMPLE 5

5-Cyano-1-(1,1-dimethylbutyl)-1H-pyrazole-4-carboxylic acid ethyl ester

2-Methyl-1-pentene (6.1 g; 0.072 mole), 3(5)-cyano-1H-pyrazole-4-carboxylic acid ethyl ester (6.0 g; 0.036 mole), and sulfuric acid (5 drops) were combined in 15 ml of acetonitrile and placed in a sealed tube. The solution was heated to 120° C. and stored at that temperature for about 8 hours. After 8 hours the solution was cooled and the acetonitrile removed under reduced pressure.

The resulting oil was purified by HPLC using hexane as eluent followed by ethyl acetate/hexane (1:4). The solvent was removed under reduced pressure to provide 4.57 g (50.9% yield) of 5-cyano-1-(1,1-dimethylbutyl)-1H-pyrazole-4-carboxylic acid ethyl ester.

Analysis calc. for $C_{13}H_{19}N_3O_2$:
Theory: C, 62.63; H, 7.68; N, 16.85;
Found: C, 62.70% H, 7.47; N, 16.76.

EXAMPLE 6

5-Cyano-1-(1,1-diethylpropyl)-N-methyl-1H-pyrazole-4-carboxamide

Sulfuric acid (4.7 g; 0.048 mole) was added dropwise to a solution containing 8.0 g (0.048 mole) of 3(5)-cyano-1H-pyrazole-4-carboxylic acid ethyl ester and 9.5 g (0.096 mole) of 3-ethyl-2-pentene dissolved in 40 ml of methylene chloride and 10 ml of acetonitrile. The acid was added at a rate such that the temperature of the solution was maintained below 10° C. throughout the addition. The reaction mixture was warmed to room temperature (25° C.) and stirred for about 16 hours.

After 16 hours an additional 100 ml of methylene chloride were added. The solution was washed twice with 150 ml of 2N sodium hydroxide and 150 ml of a saturated brine solution, then dried using sodium sulfate. The methylene chloride and acetonitrile were removed under reduced pressure to provide an oil.

This oil was purified by HPLC using hexane followed by ethyl acetate/hexane (1:4) as eluent. The solvent was again removed under reduced pressure providing 6.3 g (49.9% yield) of 5-cyano-1-(1,1-diethylpropyl)-1H-pyrazole-4-carboxylic acid ethyl ester.

Analysis calc. for $C_{14}H_{21}N_3O_2$:
Theory: C, 63.85; H, 8.04; N, 15.96;
Found: C, 64.09; H, 7.98; N, 16.26.

The above carboxylic acid ethyl ester (2.5 g; 9.5 mmole) and aqueous methylamine (4.5 g of a 40%, by weight, solution of methylamine in water; 57.0 mmole) were combined in 50 ml of methanol. The solution was heated at reflux for 8 hours then cooled to room temperature (25° C.)

The solution was concentrated by removal of unreacted methylamine and methanol under reduced pressure. The resulting solid was recrystallized from toluene/hexane to provide 0.58 g (26.4% yield) of 5-cyano-1-(1,1-diethylpropyl)-N-methyl-1H-pyrazole-4carboxamide. m.p. 85-87° C.

Analysis calc. for $C_{13}H_{20}N_4O$:
Theory: C, 62.88; H, 8.12; N, 22.56;
Found: C, 62.63; H, 7.99; N, 22.30.

EXAMPLE 7

5-Cyano-1-(1-methylcyclopentyl)-N-methyl-1H-pyrazole-4-carboxamide

Zinc chloride (13.2 g; 0.096 mole), 1-methyl-1-cyclopentene (8.0 g; 0.096 mole), and 3(5)-cyano-1H-pyrazole-4-carboxylic acid ethyl ester (8.0 g; 0.048 mole) were added to 50 ml of acetonitrile and the mixture refluxed for about 24 hours. After 24 hours the solution was cooled to room temperature (25° C.) and the zinc chloride removed by filtration. The filtrate was concentrated to an oil by solvent removal under reduced pressure.

Water (200 ml) and ethyl acetate (200 ml) were added to dissolve the oil. The organic layer was separated, washed twice with 150 ml of 2N sodium hydroxide and 150 ml of a saturated brine solution, and then dried using sodium sulfate. The ethyl acetate was removed under reduced pressure to provide an oil.

This oil was purified by HPLC per the method described in Example 5. The solvent was again removed under reduced pressure to provide 4.2 g (35.4% yield) of 5-cyano-1-(1-methylcyclopentyl)-1H-pyrazole-4carboxylic acid ethyl ester.

Analysis calc. for $C_{13}H_{17}N_3O_2$:
Theory: C, 63.14; H, 6.93; N, 16.99;
Found: C, 63.36; H, 6.73; N, 16.72.

The above carboxylic acid ethyl ester (2.0 g; 8.0 mmole) and aqueous methylamine (3.6 g of a 40%, by weight, solution of methylamine in water; 48.5 mmole) were combined in 30 ml of methanol. The solution was heated at reflux for 7 hours then cooled to room temperature (25° C.)

Methanol and unreacted methylamine were removed under reduced pressure. The resulting solid was recrystallized from ethanol to provide 1.3 g (70.0% yield) of 5-cyano-1-(1-methylcyclopentyl)-N-methyl-1H-pyrazole-4-carboxamide. m.p. 139-141° C.

Analysis calc. for $C_{12}H_{16}N_4O$:
Theory: C, 62.05: H, 6.94; N, 24.12;
Found: C, 61.83: H, 6.95: N, 23.93.

We claim:

1. A process for preparing 1-tertiary alkyl-5-cyano-1H-pyrazole-4-carboxylic acid esters of the formula

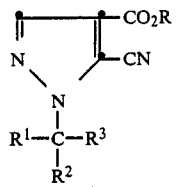

wherein:

R is $C_1$–$C_6$ alkyl; $R^1$ is $C_1$–$C_4$ alkyl; and $R^2$ and $R^3$ independently are $C_1$–$C_3$ alkyl, or when combined with the carbon atom to which they are attached form a $C_5$–$C_6$ cycloalkyl; with the proviso that when $R^2$ and $R^3$ are independently $C_1$–$C_3$ alkyl the total number of carbon atoms contained in $R^1$, $R^2$ and $R^3$ is $C_3$–$C_7$, comprising reacting a 3(5)-cyano-1H-pyrazole-4-carboxylic acid ester of the formula

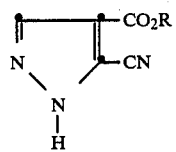

with a $C_4$–$C_8$ alkene, or a $C_5$–$C_6$ cycloalkene substituted at the 1-position with a $C_1$–$C_4$ alkyl group, and a strong acid, in a solvent which has a nitro or nitrile group.

2. A process of claim 1 employing isobutylene (2-methyl-1-propene), 2-methyl-1-pentene, 3-ethyl-2-pentene, or 1-methyl-1-cyclopentene as the $C_4$–$C_8$ alkene or the $C_5$–$C_6$ substituted cycloalkene.

3. The process of claim 1 employing isobutylene (2-methyl-1-propene) as the $C_4$–$C_8$ alkene.

4. The process of claim 1 employing 3(5)-cyano-1H-pyrazole-4-carboxylic acid ethyl ester.

5. The process of claim 2 employing 3(5)-cyano-1H-pyrazole-4-carboxylic acid ethyl ester.

6. The process of claim 3 employing 3(5)-cyano-1H-pyrazole-4-carboxylic acid ethyl ester.

7. The process of claim 1 employing p-toluenesulfonic acid as the strong acid.

8. The process of claim 2 employing p-toluenesulfonic acid as the strong acid.

9. The process of claim 3 employing p-toluenesulfonic acid as the strong acid.

10. The process of claim 1 employing sulfuric acid as the strong acid.

11. The process of claim 2 employing sulfuric acid as the strong acid.

12. The process of claim 3 employing sulfuric acid as the strong acid.

13. The process of claim 1 employing acetonitrile as the solvent.

14. The process of claim 2 employing acetonitrile as the solvent.

15. The process of claim 3 employing acetonitrile as the solvent.

16. A process of claim 1 employing isobutylene as the $C_4$–$C_8$ alkene, p-toluenesulfonic acid as the strong acid, and acetonitrile as the solvent.

17. The process of claim 1 employing isobutylene as the $C_4$–$C_8$ alkene, sulfuric acid as the strong acid, and acetonitrile as the solvent.

18. The process of claim 1 comprising reacting 3(5)-cyano-1H-pyrazole-4-carboxylic acid ethyl ester with isobutylene and p-toluenesulfonic acid in acetonitrile.

* * * * *